United States Patent
Menon et al.

(10) Patent No.: US 11,744,561 B2
(45) Date of Patent: Sep. 5, 2023

(54) SALIVA COLLECTION AND TESTING SYSTEM

(71) Applicant: Smylio Inc., Fremont, CA (US)

(72) Inventors: Renjith Menon, Campbell, CA (US); Loc Phan, Santa Clara, CA (US); Nichole Garcia, Laguna Beach, CA (US)

(73) Assignee: Smylio Inc., Fremont, CA (US)

( * ) Notice: Subject to any disclaimer, the term of this patent is extended or adjusted under 35 U.S.C. 154(b) by 132 days.

(21) Appl. No.: 17/092,262

(22) Filed: Nov. 7, 2020

(65) Prior Publication Data

US 2021/0137503 A1    May 13, 2021

Related U.S. Application Data

(60) Provisional application No. 62/932,396, filed on Nov. 7, 2019.

(51) Int. Cl.
*A61B 10/00* (2006.01)
*A61B 5/00* (2006.01)
*A61B 5/145* (2006.01)

(52) U.S. Cl.
CPC ...... *A61B 10/0051* (2013.01); *A61B 5/14507* (2013.01); *A61B 5/14539* (2013.01);
(Continued)

(58) Field of Classification Search
CPC ............ A61B 10/0051; A61B 5/14507; A61B 5/14539; A61B 5/14546; A61B 5/4875; A61B 5/682; A61B 2560/04; A61B 5/00; A61B 5/145; A61B 5/14551; A61B 5/14552; A61B 5/14532; A61C 19/04; A61C 7/08

See application file for complete search history.

(56) References Cited

U.S. PATENT DOCUMENTS

| | | | |
|---|---|---|---|
| 4,629,424 | A | 12/1986 | Lauks et al. |
| 5,079,080 | A | 1/1992 | Schwarz |

(Continued)

FOREIGN PATENT DOCUMENTS

| | | |
|---|---|---|
| WO | 2001001025 A2 | 1/2001 |
| WO | 2001042339 A1 | 6/2001 |

(Continued)

OTHER PUBLICATIONS

Anastasova S. et al.; A wearable multisensing patch for continuous sweat monitoring; Biosens Bioelectron; Jul. 15, 2017; 93:139-145; doi: 10.1016/j.bios.2016.09.038; Epub Sep. 21, 2016; Erratum in: Biosens Bioelectron; Aug. 15, 2017; 94:730; PMID: 27743863.

(Continued)

*Primary Examiner* — Chu Chuan Liu
(74) *Attorney, Agent, or Firm* — MT HUNT LAW; Marcus T. Hunt

(57) ABSTRACT

A system with a saliva sampling device configured to be orally worn by a patient. The saliva sampling device is a polymer retainer or aligner. A saliva analysis engine is used to correlate one or more analytes of one or more saliva samples with one or more health attributes. A health monitoring engine updates a health profile of the patient based on the correlated health attributes.

20 Claims, 6 Drawing Sheets

(52) U.S. Cl.
CPC ........ *A61B 5/14546* (2013.01); *A61B 5/4875* (2013.01); *A61B 5/682* (2013.01); *A61B 2560/04* (2013.01)

(56) References Cited

U.S. PATENT DOCUMENTS

| | | | |
|---|---|---|---|
| 5,942,056 | A | 8/1999 | Singh |
| 5,975,893 | A | 11/1999 | Chishti et al. |
| 6,450,807 | B1 | 9/2002 | Chishti et al. |
| 6,508,988 | B1 | 1/2003 | Dam et al. |
| 6,841,229 | B2 | 1/2005 | Sun et al. |
| 7,444,308 | B2 | 10/2008 | Guyon et al. |
| 7,812,082 | B2 | 10/2010 | Mcintosh et al. |
| 7,855,315 | B2 | 12/2010 | Mitchell et al. |
| 9,679,104 | B2 | 6/2017 | Rooyen et al. |
| 10,100,356 | B2 | 10/2018 | Esfandyarpour et al. |
| 11,313,804 | B2 | 4/2022 | Lura et al. |
| 2003/0138829 | A1 | 7/2003 | Unger et al. |
| 2009/0123886 | A1* | 5/2009 | Vaska ............... A61F 5/566 433/91 |
| 2011/0301027 | A1 | 12/2011 | Bitis et al. |
| 2016/0026917 | A1 | 1/2016 | Weisberg et al. |
| 2016/0367188 | A1* | 12/2016 | Malik ............... A61B 5/682 |
| 2017/0290545 | A1* | 10/2017 | Zerick ............... A61B 5/742 |
| 2018/0256103 | A1* | 9/2018 | Cole ............... A61B 5/14546 |
| 2018/0368961 | A1 | 12/2018 | Shanjani et al. |
| 2019/0175104 | A1* | 6/2019 | Malik ............... A61B 10/0051 |
| 2019/0223751 | A1 | 7/2019 | Weinstein et al. |
| 2019/0254579 | A1* | 8/2019 | Heikenfeld ........ A61B 5/14503 |

FOREIGN PATENT DOCUMENTS

| | | | |
|---|---|---|---|
| WO | 2002043615 | A2 | 6/2002 |
| WO | WO-2018104835 | A1 * | 6/2018 ......... A61B 5/14532 |
| WO | 2019217764 | A1 | 11/2019 |
| WO | 2020223380 | A1 | 11/2020 |

OTHER PUBLICATIONS

Bunyakul N. et al.; Combining electrochemical sensors with miniaturized sample preparation for rapid detection in clinical samples; Sensors (Basel); Dec. 30, 2014; 15(1):547-64; doi: 10.3390/s150100547; PMID: 25558994; PMCID: PMC4327035.
Dominguez RB et al.; The Evaluation of a Low-Cost Colorimeter for Glucose Detection in Salivary Samples; Sensors (Basel); Nov. 1, 2017; 17(11):2495; doi: 10.3390/s17112495; PMID: 29104212; PMCID: PMC5713636.
Domínguez-Renedo O. et al.; Disposable electrochemical biosensors in microbiology; Current research, technology and education topics in applied microbiology and microbial biotechnology; 1462-1470; 2010.
Ilea A et al.; Saliva, a Magic Biofluid Available for Multilevel Assessment and a Mirror of General Health—A Systematic Review; Biosensors (Basel); Feb. 14, 2019; 9(1):27; doi: 10.3390/bios9010027; PMID: 30769890; PMCID: PMC6468816.
Kaczor-Urbanowicz KE et al.; Emerging technologies for salivaomics in cancer detection; J Cell Mol Med. Apr. 2017; 21(4):640-647; doi: 10.1111/jcmm.13007; Epub Nov. 13, 2016; PMID: 27862926; PMCID: PMC5345659.
Kim J et al.; Non-invasive mouthguard biosensor for continuous salivary monitoring of metabolites; Analyst; Apr. 7, 2014; 139(7):1632-6; doi: 10.1039/c3an02359a; PMID: 24496180.

Kim J et al.; Wearable salivary uric acid mouthguard biosensor with integrated wireless electronics; Biosens Bioelectron; Dec. 15, 2015; 74:1061-8; doi: 10.1016/j.bios.2015.07.039; Epub Aug. 1, 2015; PMID: 26276541; PMCID: PMC4718709.
Lee EK et al.; Skin-Mountable Biosensors and Therapeutics: A Review; Annu Rev Biomed Eng. Jun. 4, 2019; 21:299-323; doi: 10.1146/annurev-bioeng-060418-052315; Epub Mar. 18, 2019; PMID: 30883212.
Lee Y et al.; Wireless, intraoral hybrid electronics for real-time quantification of sodium intake toward hypertension management; Proc Natl Acad Sci USA; May 22, 2018; 115(21):5377-5382; doi: 10.1073/pnas.1719573115; Epub May 7, 2018; PMID: 29735689; PMCID: PMC6003521.
Loo JA et al.; Comparative human salivary and plasma proteomes; J Dent Res. Oct. 2010; 89(10):1016-23; doi: 10.1177/0022034510380414; Epub Aug. 25, 2010; PMID: 20739693; PMCID: PMC3144065.
Lorenzo-Pouso AI et al.; Protein-Based Salivary Profiles as Novel Biomarkers for Oral Diseases; Dis Markers; Nov. 7, 2018; 2018:6141845; doi: 10.1155/2018/6141845; PMID: 30524521; PMCID: PMC6247606.
Malon RS et al.; Saliva-based biosensors: noninvasive monitoring tool for clinical diagnostics; Biomed Res Int. 2014; 2014:962903; doi: 10.1155/2014/962903; Epub Sep. 8, 2014; PMID: 25276835; PMCID: PMC4172994.
Santana-Jiménez LA et al.; Naked-Eye Detection of Glucose in Saliva with Bienzymatic Paper-Based Sensor; Sensors (Basel); Apr. 3, 2018; 18(4):1071; doi: 10.3390/s18041071; PMID: 29614003; PMCID: PMC5948659.
Wei F et al.; Point-of-care platforms for salivary diagnostics; Chin J Dent Res. 2012; 15(1):7-15; PMID: 22866276.
Yeh CK et al.; Current development of saliva/oral fluid-based diagnostics; Tex Dent J. Jul. 2010; 127(7): 651-61; PMID: 20737986; PMCID: PMC3742318.
Al-Muhtaseb, S. I. "Serum and saliva protein levels in females with breast cancer", Oncology Letters 8.6 (2014): 2752-2756.
Alonso-Lomillo M.A. et al. "Screen-printed biosensors in microbiology; A review." Talanta 2010;82:1629-1636.
Ballesta Claver, J. "Disposable electrochemiluminescent biosensor for lactate determination in saliva." Analyst 2009, 134, 1423-1432.
Bang G. et al., "On-Chip Lipid Extraction Using Superabsorbent Polymers for Mass Spectrometry." Anal. Chem. Dec. 19, 2017;89(24):13365-13373.
Camarena et al., "An Optimized Centrifugal Method for Separation of Semen from Superabsorbent Polymers for Forensic Analysis" J Forensic Sci, 62: 411-416.
Jansson Godoy, Nina; International Search Report & Written Opinion for PCT/US2020/059582 with international filing date of Nov. 7, 2020; dated Feb. 23, 2021.
Loo et al. "Comparative human salivary and plasma proteomes." Journal of dental research vol. 89, 10 (2010): 1016-23.
Loo et al., Supra; Ilea, Aranka et al. "Saliva, a Magic Biofluid Available for Multilevel Assessment and a Mirror of General Health—A Systematic Review." Biosensors vol. 9,1 27. Feb. 14, 2019.
Mishra et al. "Recent advances in salivary cancer diagnostics enabled by biosensors and bioelectronics." Biosensors & Bioelectronics 2016;81:181-197.
Yoshizawa et al. "Salivary biomarkers: toward future clinical and diagnostic utilities." Clinical microbiology reviews vol. 26,4 (2013): 781-91.

* cited by examiner

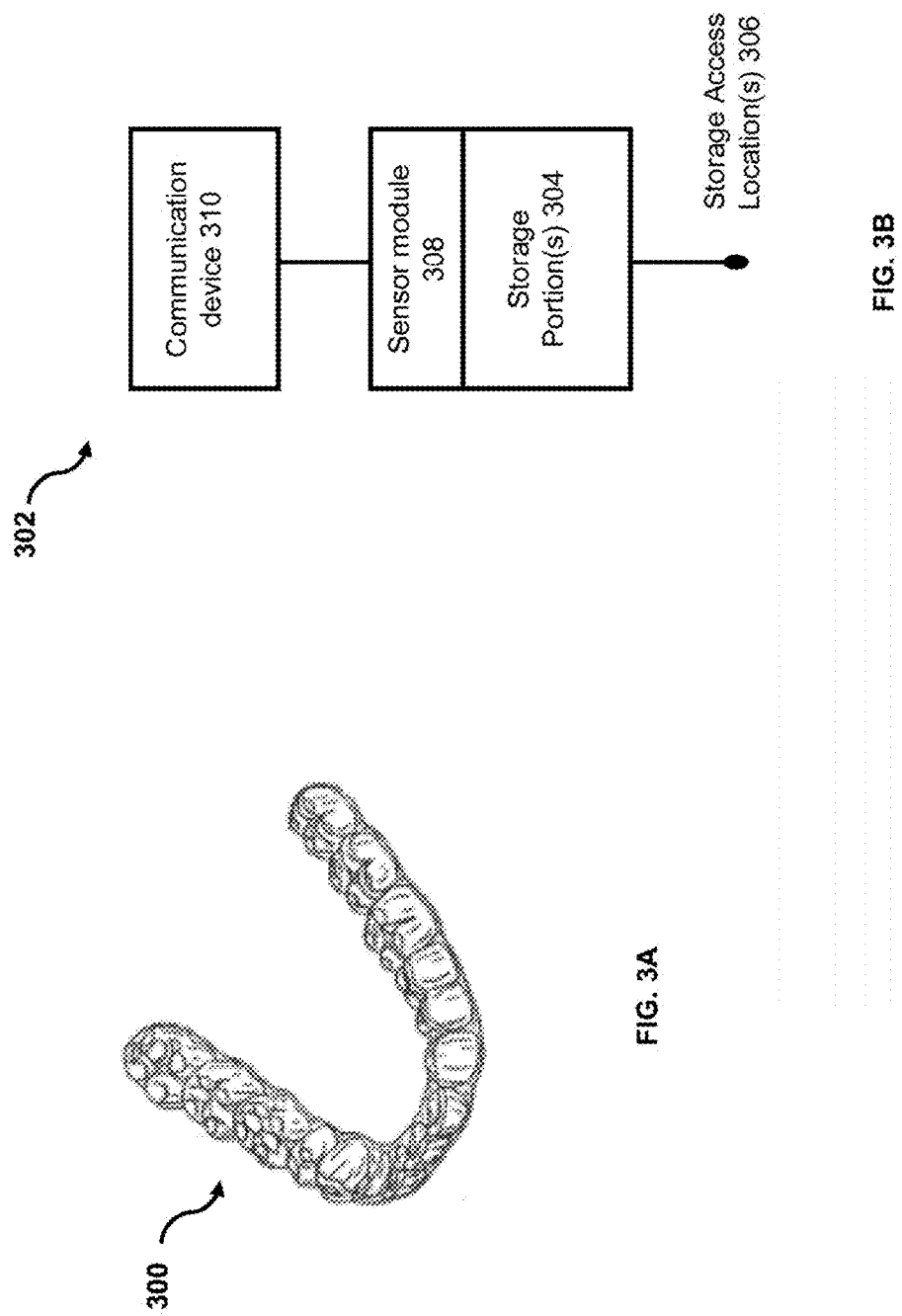

SALIVA COLLECTION AND TESTING SYSTEM

CROSS-REFERENCE TO RELATED APPLICATIONS

This application claims the benefit of U.S. Provisional Application No. 62/932,396, filed Nov. 7, 2019, which is incorporated by reference herein.

BACKGROUND

Recent and continuing advances, in fields of proteomics for example, have led to the discovery of new fluid-borne biomarkers for prediction and diagnosis of various diseases. Blood is the traditional fluid of biomarker testing for many pathologies. Blood samples, however, can be difficult to process, particularly when attempting to isolate of an analyte of interest, such as a particular protein. Often relatively large blood samples are needed because of filtration and separation steps in the process. In addition, many patients are reluctant to have blood samples taken due to negative reactions associated with needle draws.

Other bodily fluids, such as urine and saliva, can include biomarkers as well. Saliva in particular has been the subject of many research fronts for the purpose of identifying new biomarkers. Notably, one publication reported that 2290 different proteins in saliva has been compiled, and that nearly 40% of the proteins, which have been hypothesized as biomarkers for diseases such as cancer, cardiovascular disease, and stroke, can be found in saliva. See Loo et al. "Comparative human salivary and plasma proteomes." *Journal of dental research* vol. 89, 10 (2010): 1016-23.

Providing saliva samples is a relatively simple process of spitting into a tube or swabbing the mouth. Because needles are not required to provide the sample, most patients do not have the same negative reactions when providing saliva samples as compared to blood samples. In many cases, patients can provide saliva samples outside of the point of care. For example, publicly accessible genetic testing companies, such as 23andme™, use saliva for genetic testing by providing customers with mailable spit tubes.

With respect to some saliva-borne analytes, due to how saliva is continually generated, saliva is considered a "real-time" fluid that represents health status at the time of collection, as opposed to blood which circulated in a closed system. Al Muhtaseb "Serum and saliva protein levels in females with breast cancer." *Oncology Letters* 8.6 (2014): 2752-2756. Hence, a particular saliva sample may not provide a high level of confidence of overall health due to when the sample was taken. Spitting into collection tubes or collecting mouth swabs, however, at regular time periods may be intrusive and present compliance issues with patients. Therefore, it would be useful to have a means to sample saliva over an extended basis with little interaction required from the patient.

SUMMARY OF THE INVENTION

Embodiments are disclosed for systems, methods and devices for tracking patient wellness using a saliva sampling device, which can sample saliva over an extended time period.

Some embodiments relate to a method where at least one analyte of at least one saliva sample can be correlated with at least one health attribute. The saliva can be collected from a saliva sampling device configured to be orally worn by a patient. A health profile of the patient can be updated based on the at least one health attribute.

Some embodiments relate to a system than can include a saliva analysis engine, which can be configured to correlate at least one analyte of at least one saliva sample with at least one health attribute.

In some embodiments, saliva can be collected from a saliva sampling device configured to be orally worn by a patient.

In some embodiments, a health monitoring engine can be configured to update a health profile of the patient based on the at least one health attribute received from the saliva analysis engine.

In some embodiments, a health profile can include at least one profile for at least one health condition, and at least one health attribute can be used to update the at least one status profile.

In some embodiments, a health profile can include at least one risk profile for at least one disease, and at least one correlated attribute can be used to update the at least one risk profile.

In some embodiments, a health profile can include at least one nutrition profile for at least one nutritional aspect, and at least one health attribute can be used to update the at least one at least one nutrition profile.

In some embodiments, at least one saliva sample can be collected by the saliva sampling device over an extended wearing period of the saliva sampling device by the patient.

In some embodiments, at least one saliva sample can be collected by the saliva sampling device over a plurality of days during incremental wearing periods of the saliva sampling device by the patient.

In some embodiments, each period of an incremental wearing periods can be at least one hour.

In some embodiments, at least one saliva sample can be one of a plurality of saliva samples collected by the saliva sampling device over a plurality of days.

In some embodiments, at least one health attribute can be processed to provide one or more of: nutritional information, disease information, hormone information, wellness information, and genetic information.

In some embodiments, nutritional information can include one or more of: hydration information, PH level information, fluoride information, mineralization information, alcohol information, and microbiome information.

In some embodiments, disease information can include one or more of: infectious disease information, cancer information, inflammation information, and/or virus information.

In some embodiments, disease information can include body function condition indicators such as hydration level and cellular osmotic conditions.

In some embodiments, a relative functioning level of various system of the body can also be indicated by a saliva biomarker.

In some embodiments, at least one health attribute can include condition indicators for hydration level.

In some embodiments, at least one health attribute can include condition indicators for cellular osmotic conditions.

In some embodiments, at least one health attribute can include condition indicators for digestive system wellness.

In some embodiments, at least one analyte can represent at least one biomarker of at least one saliva sample.

In some embodiments, at least one analyte can be received from a saliva testing system configured to test the at least one saliva sample for presence of at least one analyte.

In some embodiments, a saliva sampling device can wirelessly transmit data to a saliva analysis engine, and the data can be indicative or non-indicative of at least one analyte.

In some embodiments, a genetics engine can be configured to correlate at least one analyte of at least one saliva sample with at least one genetic attribute.

In some embodiments, a records engine can store the health profile.

In some embodiments, health monitoring engine can be configured to provide health monitoring updates and/or alerts to at least one access device.

In some embodiments, a health monitoring engine can be configured to identify one or more health conditions and provide recommendations about products and/or medications to address the one or more health conditions.

In some embodiments, a saliva sampling device can include one of: a retainer and an aligner.

In some embodiments, a saliva sampling device can be one of a plurality of saliva sampling devices.

In some embodiments, a health profile can be updated and maintained from a plurality of correlated health attributes derived from a plurality of saliva samples collected by the plurality of saliva sampling devices.

In some embodiments, a saliva sampling device can include at least one sensor.

In some embodiments, a saliva sampling device can include at least one biosensor.

In some embodiments, a saliva wherein the saliva sampling device can include one or more saliva storage portions configured to store the saliva over.

In some embodiments, at least one sensor can be configured to detect a biomarker.

In some embodiments, a saliva sampling device can include at least one sensor and at least one communication device coupled to the sensor.

In some embodiments, at least one communication device can be configured to wirelessly connect with a network and/or a network access device.

In some embodiments, a saliva sampling device can be shaped to fit onto surfaces of a set of teeth.

In some embodiments, a sampling device can be configured to collect and store saliva over a plurality of days.

In some embodiments, a saliva sampling device can include at least one microfluidic channel.

In some embodiments, a saliva sampling device can include at least one microfluidic chamber.

In some embodiments, a saliva sampling device can include at least one microfluidic pump.

In some embodiments, a saliva sampling device can include an absorbent material.

In some embodiments, an absorbent material can include at least one absorbent member.

In some embodiments, an absorbent material can include a plurality of absorbent members.

In some embodiments, an absorbent material can include a membrane, paper, cloth, superabsorbent polymer, and/or a hydrogel.

In some embodiments, a saliva sampling device can include a base layer shaped to fit over a set of teeth, and a sampling layer shaped to fit the base layer and configured to collect saliva.

In some embodiments, a saliva sampling device can include a top layer shaped to fit over the sampling layer.

In some embodiments, a saliva sampling device can include at least one electrical circuit.

In some embodiments, at least one electrical circuit can be triggered by detection of a biomarker.

In some embodiments, a saliva sampling device can include a communication device.

In some embodiments, a saliva sampling device can be adapted to provide an alert when triggered by the detection of a biomarker.

In some embodiments, a saliva sample contains biomarkers regarding the human reproductive system.

In some embodiments, biomarkers can be correlated for pregnancy determination, sex of a fetus, wellness of the fetus, ovulation status of patient, and fertility status of patient.

BRIEF DESCRIPTION OF THE DRAWINGS

Reference will be made to the following Detailed Description, which is to be read in conjunction with the accompanying drawings, wherein according to some embodiments:

FIG. 3A. illustrates a projected view of a saliva sampling device, according to some embodiments;

FIG. 3B illustrates a schematic drawing of a saliva sampling device, according to some embodiments;

Figure 1:
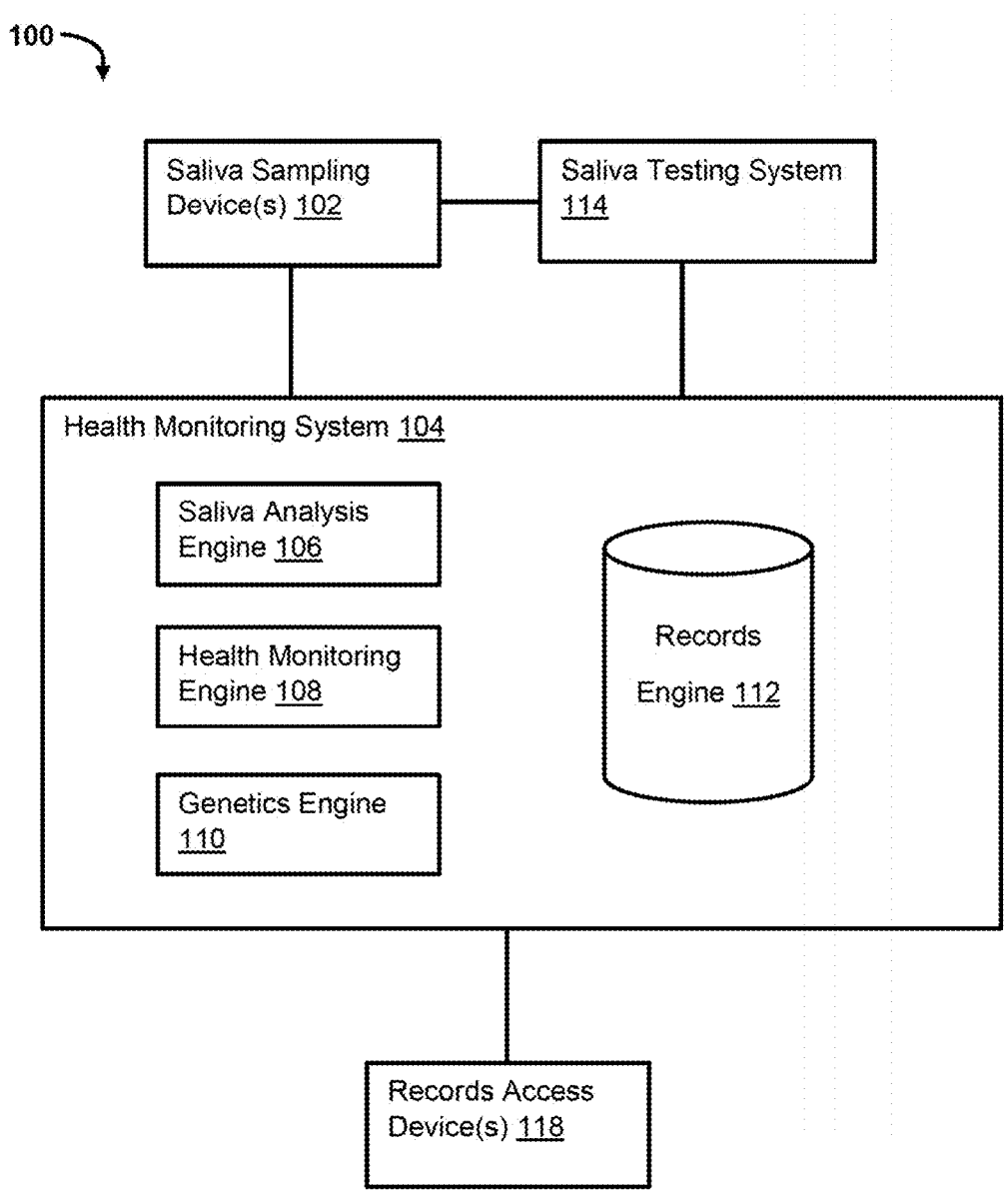
FIG. 1 illustrates a schematic drawing of a salivary sampling and testing system, according to some embodiments.

The figures depict various embodiments of the present invention for purposes of illustration only, wherein the figures use like reference numerals to identify like elements. One skilled in the art will readily recognize from the following discussion that alternative embodiments of the structures and methods illustrated in the figures can be employed without departing from the principles of the invention described herein.

DETAILED DESCRIPTION

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range.

Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order that is logically possible.

FIG. 1 illustrates system 100 for maintaining a health profile of a patient based on saliva sampling. System 100 includes one or more saliva sampling devices 102, which can be configured to sample saliva from a patient while being worn orally. In some embodiments, saliva sampling device 102 is configured to perform more than one primary function. For example, saliva sampling device 102 can include the basic structure of a teeth mountable orthodontic polymer aligner (e.g. INVISALIGN aligner) or a teeth mountable orthodontic polymer retainer (e.g. ESSIX ACE). The advantage of saliva sampling device 102 having two functions is that the patient will be wearing saliva sampling device 102 for an extended period of time (e.g., greater than 1 hour, 1-8 hours, etc.) on a continuing basis (i.e., daily, semi-daily) for personal health or appearance reasons. Therefore, patient wear compliance is likely to be greater when saliva sampling device 102 is incorporated into a multi-function device, because the patient is following an orthodontic regimen.

In some embodiments, a patient does not require orthodontic therapy, but wishes to use saliva sampling device 102. For such patients, a retainer or aligner can be constructed on the current state of the patient's tooth position. Although such a saliva sampling device 102 does not have a secondary function to move or retain tooth position, for the purposes of this disclosure such a saliva sampling device 102 can still be referred to as a retainer and/or aligner.

Some embodiments of saliva sampling device 102 are configured to collect one or more saliva samples over an extended period of time. In some embodiments, saliva sampling device 102 can collect a discrete sample of saliva that corresponds to a particular wearing period. Put another way, each time saliva sampling device 102 is worn, it can collect a separated sample or a single sample. In some embodiments, saliva sampling device 102 can collect a continuous sample of saliva that is non-discretely stored within saliva sampling device 102. Put another way, each time saliva sampling device 102 is worn it can incrementally add saliva to a collection reservoir that is configured to be filled slowly over time, such that the resulting saliva sample is an aggregate of multiple sampling periods.

Some embodiments of saliva sampling device 102 include one or more of: channels, microfluidic channels, chambers, microfluid chambers, absorbent materials, preservatives, chemical and/or drug reservoirs, pumps, processors, sensors, biosensors, and communication devices. Specific aspects of saliva sampling device 102 are disclosed below.

In some embodiments, saliva sampling device 102 is one of a plurality of saliva sampling devices used on an on-going basis for tracking patient wellness. Accordingly, in some embodiments, saliva sampling device 102 can be returned for testing to a care provider after a wear period (e.g. 1-2 months) and a new saliva sampling device can then be worn by the patient. This can be performed indefinitely so as to provide wellness tracking over the patient's life time.

System 100 can include multiple submodules and/or subsystems, which for the sake of simplicity can be referred to as modules. Such modules can be implemented using hardware, firmware, and/or software embodied on a non-transitory computer-readable medium that is executed by underlying hardware, such as one or more processors. For example, such modules can represent code that is embodied on a non-transitory computer-readable medium and directs the processor of system 100 to perform corresponding actions. Such modules can include: health monitoring system 104, saliva analysis engine 106, health monitoring engine 108, genetics engine 110, records engine 112, saliva testing system 114, and records access devices 116. Modules can be considered to be optional, addable, and/or or removable from system 100. For example, in some embodiments, records access device 118 is not required for health monitoring system 104 to function. Likewise, in some embodiments, saliva testing system 114 is only used for saliva sampling devices 102 lacking sensors and/or communication devices.

Health monitoring system 104 can be configured to receive data, which can be raw data sent by saliva sampling device 102 and/or processed data from saliva testing system 114, correlate the processed data with one or more health attributes, and maintain a health profile of a patient by updating the health profile with the health attributes. In some embodiments, health monitoring system 104 can correlate the processed data with one or more genetic attributes and maintain a health profile of a patient by updating the health profile with the genetic attributes. Health monitoring system 104 can include one or more engines, such as saliva analysis engine 106, health monitoring engine 108, genetics engine 110, and records engine 112.

If not already processed by saliva testing system 114, data can be processed by saliva analysis engine 106 to determine the type, presence, relative concentration, ratio, and/or quantity of one or more analytes, which can function as biomarkers. In some embodiments, a multiplex of analytes can be identified. Such analytes can include proteins, cytokines, chemokines, interleukin 6, interleukin 1 beta, tumor necrosis factor alpha, C-reactive protein, transferrin, histamine, histatin, cells, molecules, alcohol, nanoparticles, chemicals, bacteria, enzymes, drugs, anti-bodies, metals, minerals, deoxyribonucleic acid (DNA), ribonucleic acid (RNA), viruses, peptides, hormones, chromogranin A, cortisol, melatonin, testosterone, amylase, alpha-amylase, cotinine, neopterin, estrogens, estradiol, estriol, estrone, dinoprostone, insulin, carbohydrate components, polysaccharides, matrix metalloproteinase-8, metallopeptidase inhibitor 1, interleukin-1 beta, interleukin-6, interleukin-8, progesterone, 17OH-progesterone, 17α-hydroxyprogesterone, aldosterone, steroids, dehydroepiandrosterone, dehydroepiandrosterone sulfate, secretory immunoglobulin A, monocyte chemoattractant protein-1, epidermal growth factor, nerve growth factor, substance P, glutamate, calcitonin gene-related peptide, brain-derived neurotrophic factor, androstenedione, oxytocin, acids, nucleic acids, lipids, uric acid, galactose, glucose, mannose, fucose microbes, biomes, electrolytes, glycoproteins, and salts.

In some embodiments, saliva analysis engine 106 can review the data collected to perform a performance and/or diagnostic analysis of saliva sampling device 102. Such analyses can include determinations of wear compliance and saliva sampling effectiveness based on the total amount of saliva collected, for example.

In some embodiments, saliva analysis engine 106 can be configured to correlate the type, presence, relative concentration, ratio, and/or quantity of one or more analytes to known biomarkers for one or more of a pathology, condition, or health status to determine one or more health attributes. Health attributes can include nutritional information, disease information, hormone information, genetic information, hydration information, PH level information, fluoride information, mineralization information, alcohol information, microbiome information, infectious disease information, cancer information, inflammation information, and/or virus information. Saliva borne biomarkers have been associated with a wide variety of diseases, viral infections, bacterial infections, parasites, physical impairment, inflammation, nutritional imbalances, hormonal imbalances, hormonal levels, menstrual cycles, adrenal disease, diabetes, asthma attacks, cancers, stress, fertility, pregnancy status, sex of a fetus, wellness of a fetus, ovulation status, fertility level, and other wellness issues.

Examples of saliva borne biomarkers are found at: Loo et al., Supra; Ilea, Aranka et al. "Saliva, a Magic Biofluid Available for Multilevel Assessment and a Mirror of General Health—A Systematic Review." *Biosensors* vol. 9, 1 27. 14 Feb. 2019; Yoshizawa et al. "Salivary biomarkers: toward future clinical and diagnostic utilities." *Clinical microbiology reviews* vol. 26, 4 (2013): 781-91; Mishra et al. "Recent advances in salivary cancer diagnostics enabled by biosensors and bioelectronics." *Biosensors & Bioelectronics* 2016; 81:181-197; and Lorenzo-Pouso, et al., "Protein-Based Salivary Profiles as Novel Biomarkers for Oral Diseases," *Disease Markers*, vol. 2018, Article ID 6141845, 22 pages, 2018, all of which are incorporated by reference.

Health monitoring engine 108 can access records engine 112 to retrieve a patient health profile and update the profile based on the one or more correlated health attributes. In some embodiments, the health profile can be a statistically based model for one or more pathologies. The health profile can be determined by one or more algorithms. The health profile can provide one or more of status, risk, likelihood, tendency, intensity, level, amount, for one or more of the health attributes. The patient health profile can include data regarding past diagnostic tests (e.g. blood/serum tests, salivary tests) records of health events, genetic information, genetic ancestry, psychological information, prescribed drug use, illicit drug use, alcohol use, smoking history, age, weight, race, environmental exposure history, and family health histories. In some embodiments, the patient health profile can be updated in parallel by other sources, for example, by wearable devices that record daily activity, heart rate, etc. In some embodiments, the patient health profile can be updated in parallel by other patient health profiles, which can be anonymized, that share similar genetic profiles, genetic ancestry, live and/or work in the same vicinity, share similar lifestyles, and/or are directly related to the patient. Some or all of these data points can be weighted and considered by system 100 when making conclusions and recommendations based on the detected biomarkers.

In some embodiments, a health profile can made up of several sub-profiles, which are derived from information based on the correlated health attributes. A sub-profile can be a statistically based model for a particular pathology. Each sub-profile can be determined by one or more algorithms. Each sub-profile can provide one or more of status, risk, likelihood, tendency, intensity, level, amount, for a health attribute. Such sub-profiles can include a nutritional profile, disease profile, hormone profile, genetic profile, hydration profile, PH profile, fluoride profile, mineralization profile, alcohol profile, microbiome profile, infectious disease profile, cancer profile, inflammation profile, and/or virus profile.

In some embodiments, saliva analysis engine 106 can be configured for performing predictive analytics to discover new biomarkers, i.e., in order to make statistical determinations on whether a particular analyte, which is not currently determined to be a biomarker, is actually a biomarker in whole or in part for a particular pathology. This can be done by analyzing data stored in access records engine 112 of a statistically relevant number of patients with saliva that test positive or negative for the same analyte (e.g., concentration, amount) and have or do not have the same corresponding pathology. This analysis can be supplemented by comparison to additional data, (e.g., lifestyle, genetics, etc.). Saliva analysis engine 106 can have an AI learning function to perform such discoveries without being commanded to. In some embodiments, this function is performed by a separate bioinformatics engine. Examples of predictive analytics systems and methodology using large data sets are disclosed in U.S. Pat. No. 7,444,308 B2; U.S. Pat. No. 9,679,104 B2; and U.S. Pub. No. 2016/0026917 A1, which are incorporated by reference herein.

In some embodiments, the health attributes can represent averaged and/or aggregated values of the attributes provided over an extended period of time, e.g., 1-60 days, 1-30 days, 1-5 days, or 6-72 hours. In some embodiments, this is due to the relatively slow and/or discrete sampling rate of saliva of saliva sampling device 102 and the relatively great amount of time saliva sampling device 102 is worn. The ability to test saliva over an extended period is potentially a major advantage over typical saliva test protocols, which test saliva biomarkers according to when the sample is physically provided by the patient at a point of care, i.e., a snap shot of wellness. Embodiments of the instant disclosure can correlate biomarkers secreted over hours, days, and/or weeks of time and without requiring the patient to visit a point of care. It has been put forth that "[s]aliva is a 'real-time' fluid due to the exocrine salivary glands that generate protein profiles, which are representative of an individual's health and well-being status at the time of collection (32). It is known that blood is contained within a closed-loop circuit, whereas the saliva is continually produced and excreted in an open-ended circuit. . . . Evaluating the whole saliva proteome in a continuous turnover environment is necessary for understanding the physiological and pathological processes that are relevant to oral health and may be critical for the identification of important biomarkers." Al Muhtaseb, Supra, which is incorporated by reference.

The scientific value of a correlated health attribute based on in vivo samples taken over an elongated sampling period is potentially great, given that access to such data is rare outside of a controlled clinical setting, such as a hospital. For example, a singular biomarker previously believed to be unreliable or non-associated with a pathology can carry more predictive weight considering the prolonged sampling period. Hence, embodiments disclosed herein can potentially be used to provide accurate diagnosis and health predictions while testing fewer types of analytes, i.e., without the need for multiplexing, therefore potentially increasing throughput, lowering complexity, and reducing risk of false positives.

Health monitoring engine 108 can update the health profile of the patent and compare the most recent data to prior health profiles. In some embodiments, health monitoring engine 108 can provide statistically weighted statuses and/or predictions of patient wellness based on the health profiles. In some embodiments, alerts for acute indications can be provided to the patient and/or a patient's caregiver so that the patient can seek immediate care. In some embodiments, a patient's health profile can be tracked to provide a life-time view of wellness. Hence, the collected data can provide a better understanding of a patient's health and disease risks, and greater emphasis can be placed on disease prevention and maintaining optimal health for the long term. In some embodiments, lifestyle changes, hormonal, nutritional, dietary, behavioral, and/or therapeutic drug therapies can be recommended by health monitoring engine 108 based on conditions predicted by the patient's health profile. In some embodiments, saliva sampling device 102 can include therapeutic aspects, such as drug delivery aspects as disclosed in Intl. App. No. PCT/US1931635, which is incorporated by reference herein.

In some embodiments, health monitoring system 104 include genetics engine 110. Genetics engine 110 can analyze and correlate DNA, RNA, nucleic acids, and/or nucleotides to provide a genetic health profile for storage on records engine 112. The genetic profile can be updated based on ongoing research that correlates genetic information to particular health conditions. The genetic profile can be correlated health attributes derived from the saliva to provide a more tailored and accurate health profile. In some embodiments, genetic ancestry can be provided to the patient based on saliva testing. In some embodiments, genetic information can be provided from a linked system that specializes in genetic testing.

In some embodiments, system 100 includes saliva testing system 114, which can include hardware and software to process saliva samples of saliva sampling device. In some embodiments, saliva testing system 114 is a point of care (POC) system. Examples of saliva-based point of care systems are discussed at Yeh "Current Development of Saliva/Oral fluid-based Diagnostics." *Tex Dent J.* 2010 July; 127(7): 651-661, which is incorporated by reference herein.

In some embodiments, saliva testing system 114 is configured to test only one type of analyte or one or more types of analytes. An analyte can be extracted from a saliva sample using techniques described by: Maniatis, et al., *Molecular Cloning: A Laboratory Manual*, Cold Spring Harbor, N.Y., pp. 280-281 (1982); and Bunyakul and Baeumner, "Combining electrochemical sensors with miniaturized sample preparation for rapid detection in clinical samples." *Sensors* (Basel, Switzerland) vol. 15, 1 547-64. 30 Dec. 2014, which are incorporated by reference.

Saliva testing system 114 can be configured to employ one or more testing methodologies, such as enzyme-linked immunosorbent assay (ELISA), polymerase chain reaction (PCR), and/or high-resolution mass spectrometry (HRMS), multiplexing, mass cytometry, single-cell genomics, DNA sequencing, RNA sequencing, and/or next generation sequencing. A potentially low cost POC technique using electrical field isolation can also be employed as described by U.S. Pat. No. 10,100,356 B2, which discloses a method for magnetically holding a bead carrying biological material (e.g., nucleic acid, which may be in the form of DNA fragments or amplified DNA) in a specific location of a substrate, and applying an electric field local to the bead to isolate the biological material or products or byproducts of reactions of the biological material, and is incorporated by reference.

Records access device 118 can access all or a portion of the patient's health profile. In some embodiments, records access device 118 is a computing device (e.g. tablet, smart phone, personal computer) of the patient or the patient's care giver. In some embodiments, records access device 118 includes access software (e.g., cloud application, mobile application) with a graphical user interface (GUI) that can be used to access the patient's health profile. In some embodiments, the access software graphically presents certain aspects of the health profile such as nutritional information, disease information, hormone information, genetic information, hydration information, PH level information, fluoride information, mineralization information, alcohol information, microbiome information, infectious disease information, cancer information, inflammation information, and/or virus information. In some embodiments, the access software is communicatively coupled to system 100 and can receive unsolicited communications from system 100, such as health alerts and updates.

Figure 2:
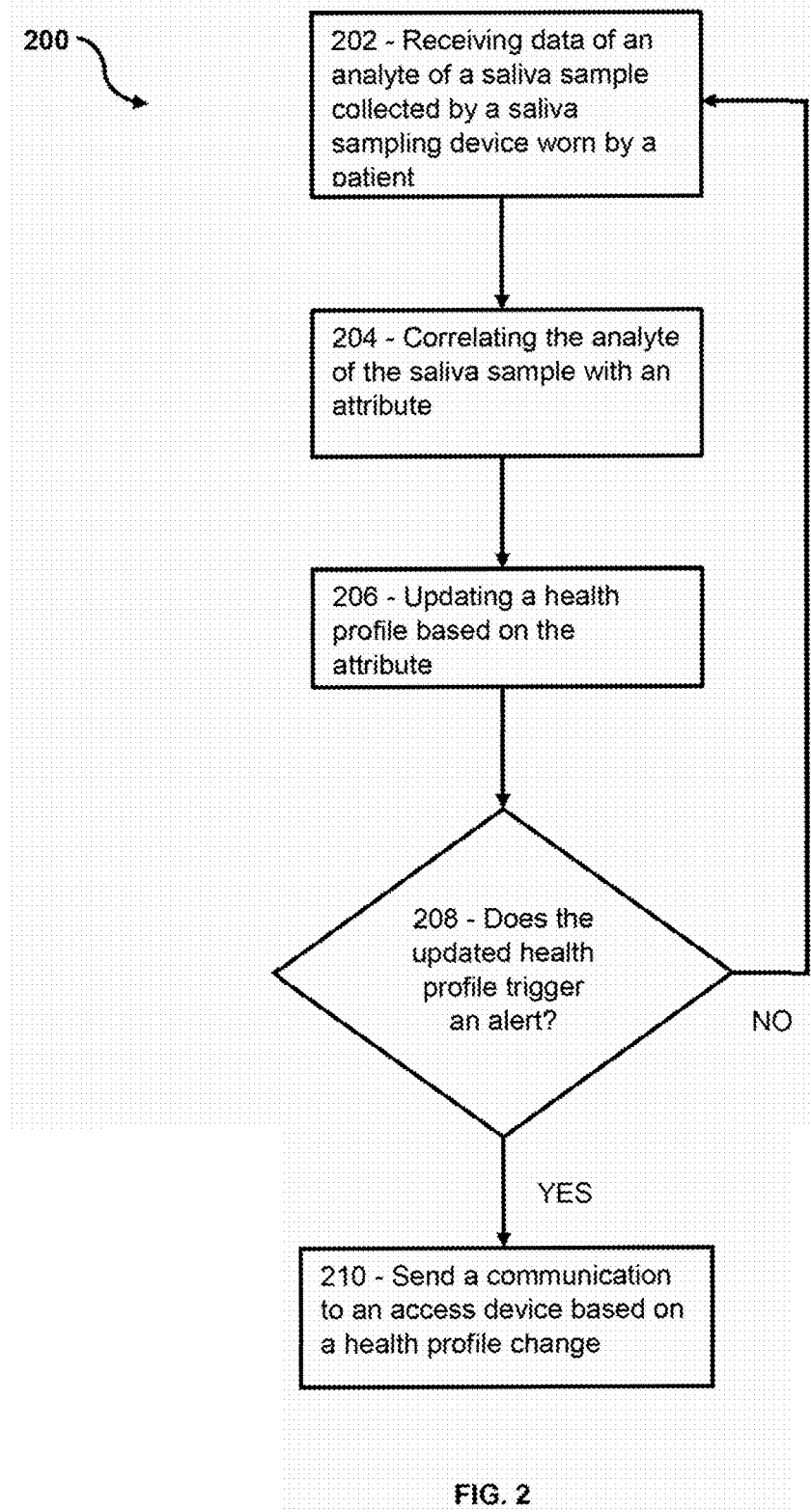
FIG. 2 illustrates a flow diagram of a method for maintaining a health profile, according to some embodiments.

FIG. 2 illustrates method 200 that can be performed by one or more processors of a system, such as system 100 and/or health monitoring system 104. Accordingly, method 200 can include some or all the aspects recited with respect to FIG. 1 not specifically recited. Method 200 can be stored as processor executable instructions on a non-transitory medium readable by the processor. The processor can be configured to execute method 200.

At operation 202, data is received regarding one or more analytes. The analytes can be sourced from one or more saliva samples collected by a saliva sampling device. The saliva samples can be collected by the saliva sampling device collected over an extended time period (e.g. a series of hours, days or weeks). In some embodiments, the saliva sample can be an aggregation of several saliva samples collected over the extended period of time into a common reservoir. In some embodiments, the saliva sample can be a plurality of discretely collected saliva samples collected over the extended period of time, where each discretely collected saliva sample corresponds to a particular wearing period of the saliva sampling device.

At operation 204, the one or more analytes of the saliva sample are correlated with one or more attributes. The attributes can include nutritional information, disease information, hormone information, genetic information, hydration information, PH level information, fluoride information, mineralization information, alcohol information, microbiome information, infectious disease information, cancer information, inflammation information, and/or virus information, as was well as several other attributes as discussed herein.

At operation 206, a health profile of the patient is updated to include the correlated one or more attributes. The heath profile can be a statistically based model for different pathologies. The health profile can provide one or more of status, risk, likelihood, tendency, intensity, level, amount, for one or more of the health attributes. The health profile can be determined by one or more algorithms.

In some embodiments, the attributes can represent averaged values of the attributes provided over the extended period of time. In some embodiments, as part of the update, the health profile can be compared to the data of prior health profiles. In some embodiments, as part of the update, statistically weighted health status, recommendations, and/or predictions of patient wellness can be derived from the updated health profile.

In some embodiments, a health profile can include sub-profiles, which are derived from information derived from the correlated attributes. A sub-profile can be a statistically based model for a particular pathology. Each sub-profile can be determined by one or more algorithms of method 200. Each sub-profile can provide one or more of status, risk, likelihood, tendency, intensity, level, amount, for a health attribute. Such sub-profiles can include a nutritional profile, disease profile, hormone profile, genetic profile, hydration profile, PH profile, fluoride profile, mineralization profile, alcohol profile, microbiome profile, infectious disease profile, cancer profile, inflammation profile, and/or virus profile. Each sub-profile can be additionally derived from data regarding past diagnostic tests (e.g. blood/serum tests, salivary tests) records of health events, genetic information, genetic ancestry, psychological information, prescribed drug use, illicit drug use, alcohol use, smoking history, age, weight, race, environmental exposure history, and family health histories.

At operation 208 it is determined whether the updated health profile triggers an alert. An alert can include advice and/or information related to one or more of nutrition, disease, hormones, genetics, hydration, PH, fluoride, mineralization, alcohol, microbiome, infectious disease, cancer, inflammation, and viruses. In some embodiments, alerts for acute or concerning indications (e.g. heart disease, cancer) can be provided to the patient and/or a patient's caregiver so that the patient can seek immediate care. Such alerts can be triggered by changes in health condition values of the health profile. If no alert is triggered, then method 200 ends or reverts to operation 202.

At operation 210, if an alert is triggered then a communication can be sent to an access device of the patient and/or the patient's care giver. In some embodiments, the access device includes access software (e.g., cloud application, mobile application) with a graphical user interface (GUI) that can be used to access the patient's health profile. The communication can be in the form of an electronic communication or application alert. In addition, if the alert is related to an acute event, a second, related alert can be triggered (e.g., causing a representative to phone a hospital, the patient, and/or the patient's care giver). In some embodiments, the access software graphically presents certain aspects of the health profile such as nutrition, disease, hormones, genetics, hydration, PH, fluoride, mineralization, alcohol, microbiome, infectious disease, cancer, inflammation, gut health, pregnancy, hydration levels, and viruses. In some embodiments, the access software is a wellness tracker that provides relative wellness levels with respect to certain aspects of the health profile such as nutrition, disease, hormones, genetics, hydration, PH, fluoride, mineralization, alcohol, microbiome, infectious disease, cancer, inflammation, gut health, pregnancy, hydration levels, and viruses.

FIG. 3A illustrates a saliva sampling device 300, according to some embodiments. Saliva sampling device 300 can be constructed similarly to a clear aligner or retainer, which are molded to fit onto teeth. A series of clear aligners can be used to incrementally adjust position of teeth from an initial arrangement to a final arrangement, and the retainer is used to maintain positioning of the teeth in the final arrangement. Clear aligners are typically worn at least 8-20 hours a day, for periods up to 9 months. Retainers are typically worn at night for 6-8 hours a day while the user is sleeping.

Clear aligners are typically constructed from a relatively flexible but resilient polymer, such as polyurethane or polyester, because the clear aligners are required to non-elastically deform to move teeth from one position to the next. Retainers are typically less flexible because application of directional force is no longer required and can therefore the retainer can be constructed from thicker polymers and/or more rigid polymers, such as polycarbonate. In some embodiments, saliva sampling device 300 can be formed from a sheet or sheets polymeric material. Saliva sampling device 300 can fit over all teeth present in an upper or lower jaw, or less than all of the teeth.

In some embodiments, only certain teeth received by saliva sampling device 300 will be repositioned by the appliance while other teeth can provide a base or anchor region for holding the appliance in place as it applies force against the tooth or teeth targeted for repositioning. Teeth that are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in saliva sampling device 300 so that the appliance can apply a selected force on the tooth. Basic methods for determining an orthodontic treatment plan using a series of incremented appliances as well as instructions for molding orthodontic appliances, are described in U.S. Pat. Nos. 6,450,807, and 5,975,893, which are incorporated by reference herein.

FIG. 3B illustrates a schematic of saliva sampling device 302, according to some embodiments. Saliva sampling device 302 can be structurally configured similarly to sampling device 300. Saliva sampling device 302 can include sample storage portion 304, storage access location(s) 306, one or more sensor modules 308, communication device 310, and processing system 312. Many aspects of saliva sampling device 302 are optional. For example, sensor module 308, communication device 310 and processing system 312 are not required for collection of saliva.

In some embodiments, the aspects of saliva sampling device 302 are micronized, e.g. microfluidic. Hence salving sampling device 302 can be configured to include structural aspects of microfluidic devices used for high throughput screening. Aspects and examples of microfluidic devices can be found at: U.S. Pat. No. 6,508,988, which describes ecombinatorial synthesis systems which rely on microfluidic flow to control the flow of reagents in a multichannel system; and U.S. Pat. No. 5,942,056, describes a microfluidic test system for performing high throughput screening assays, wherein test compounds can be flowed through a plurality of channels to perform multiple reactions contemporaneously. Additional information can be found at Unger et al. "Monolithic microfabricated valves and pumps by multilayer soft lithography." 2000, Science 288:113-116; Int.l' Pub. No. WO 01/01025; Int.l' Pub. No. WO/02/43615; and U.S. Pub. No. 20030138829. The preceding publications are incorporated by reference.

In some embodiments, sample storage portion 304 can be a portion of a sensor or biosensor, such as a bioreceptor. In some embodiments, sample storage portion 304 includes one or more of a reagent, preservative, detergent, surfactant, lysing agent, or reducing agent. In some embodiments, sample storage portion 304 can include one or more of a chamber, reservoir, channel, bead, or nanoparticle.

In some embodiments, sample storage portion 304 can include an absorbent material (e.g., paper, cloth, fibers, hydrogel, freeze-dried hydrogel, synthetic and/or natural superabsorbent polymers (e.g., polysaccharides and proteins, soy protein/poly(acrylic acid), and/or polyacrylate/polyacrylamide copolymers)). In some embodiments, a portion, or a separate portion, of the, absorbent material can be configured to dilute a therapeutic substance (e.g., drugs, minerals, vitamins, electrolytes, PH neutralizer) into the oral cavity.

In some embodiments, a synthetic and/or natural superabsorbent polymer composite can be used to avoid issues like gel blocking. An example of a superabsorbent polymer composite including a superabsorbent polymer and cellulosic fibrils with good flexibility traits is disclosed at U.S. Pub. No. 2011/0301027 A1, which is incorporated by reference. In some embodiments, a sheet of superabsorbing polymer can be used where sample storage portion 304 is in the form of a partial or complete layer. A technique for forming a water-absorbing sheet by extruding an aqueous solution of superabsorbing polymer as a fibrous stream onto a high velocity, hot fibrous stream of melt-blown fibers of thermoplastic polymer is disclosed at U.S. Pat. No. 5,079,080, the disclosure of which is incorporated by reference. A technique of forming a superabsorbent paper-like sheet is disclosed at U.S. Pat. No. 7,855,315 B2, which is incorporated by reference.

In some embodiments, sample storage portion 304 can be in the form of an absorptive coating on a substrate, such as a superabsorbing polymer coating on a thermoplastic portion of an aligner or retainer. An example of coating a thermoplastic polymer with a superabsorbent polymer composition is disclosed at U.S. Pat. No. 7,812,082 B2, which is incorporated by reference herein. An example of a superabsorbent polymers having a slow rates of water absorption are disclosed at Int'l. Pub. No. WO2001/042339 A1 and U.S. Pat. No. 6,841,229 B2, which are incorporated by reference.

Removing analytes from a superabsorbing polymer can be achieved by multiple techniques. Superabsorbing polymer have been used as lab and forensic tools to extract analytes and fluids of interest. A process for solubilizing and eluting the analyte directly into an organic solvent is described by Bang G. et al., "On-Chip Lipid Extraction Using Superabsorbent Polymers for Mass Spectrometry." *Anal. Chem.* 2017 Dec. 19; 89(24):13365-13373, which is incorporated by reference. A filtering process using a centrifuge to remove semen from a super absorbing polymer for DNA analysis is described at Camarena et al., "An Optimized Centrifugal Method for Separation of Semen from Superabsorbent Polymers for Forensic Analysis" *J Forensic Sci,* 62: 411-416, which is incorporated by reference.

In some embodiments, sample storage portion 304, and/or connecting channels there to, can be an absorptive material fully or partially coated with a hydrophobic material to slow absorption to a desired rate or prevent absorption until desired. In some embodiments, the hydrophobic material is configured to break down or fracture over time or by application of force, for example in the case of discrete sample storage portions 304 manual application of force by the patient (e.g. squeezing between fingers) of a portion of saliva sampling device 302 can ready the affected sampling storage portion 304 for saliva absorption.

In some embodiments, connecting channels to sample storage portion 304 can be partially or fully blocked with a hydrophilic material configured to break down or fracture over time or by application of force, for example by manual application of force by the patient to the blocked channel. Because the channel blocking material is hydrophilic, it can still draw in saliva even if almost fully blocked after fracturing. In some embodiments, sample storage portion 304 can be an absorptive material of relatively high mass, such that complete or desired saliva absorption is achieved by contact with saliva after an extended period of time (e.g., 1 hour, several hours, days, or weeks). In some embodiments, the relatively high mass of absorptive material can be regulated by relatively small sized saliva feeding channels.

One or more storage access location 306 provide access from the oral cavity to the one or more sample storage portions 304. In some embodiments, storage access location 306 can be an opening in a portion of saliva sampling device 302. In some embodiments, storage access location 306 can be a plurality of openings. In some embodiments, storage access location 306 can be dimensions to limit saliva intake. In some embodiments, storage access location 306 can be one or more microfluidic openings. In some embodiments, storage access location 306 can be covered with a user removable cover, which the user can remove to enable sampling at different time periods. In some embodiments, storage access location 306 can be covered with a bioabsorbable cover. In some embodiments, to provide saliva samples at different periods of time, a plurality of bioabsorbable covers can cover a plurality of discrete storage access locations 306 and have different thicknesses or properties such that the covers erode/absorb at different points during use, e.g., 1 hour, 12 hours, 48 hours, etc. In some embodiments, one or more of storage access location 306 can be located on saliva sampling device 302 to be placed most proximate to one of the parotid, submandibular, and sublingual glands when worn in the oral cavity.

Storage access location 306 can be in fluidic communication with sample storage portion 304. In some embodiments, a microfluidic pump is in fluidic communication with storage access location 306 and sample storage portion 304 and configured to move saliva from storage access location 306 to sample storage portion 304. In some embodiments, a fluidic path between storage access location 306 and sample storage portion 304 is configured to move saliva from storage access location 306 to sample storage portion 304 by use of capillary action. In some embodiments, the fluidic path includes a wicking composition, such as cellulose, cloth, hydrophilic material/coating, and/or hydrogel, to wick saliva from storage access location 306 to sample storage portion 304.

Sensor module 308 can be configured to react with a particular analyte or to halt or cause signal propagation. Sensor module 308 can include a transducer coupled to the bioreactor that reacts with the particular analyte. The reaction can cause the transducer to produce an electrical effect, such as a voltage and/or current signal. Sensor module 308 can include a signal processor configured to receive the electrical effect from the transducer and output a result, such as producing one or more digital signals that are used to indicate presence of the analyte at the bioreactor. Sensor module 308 can continuously or intermittently provide processing system 312 with an indication of the condition.

In some embodiments, sensor module 308 can be a screen-printed circuit that is directly printed onto a substrate of saliva sampling device 302 or onto a separate substrate. Examples of screen printed biosensors are disclosed at Alonso-Lomillo M. A. et al. "Screen-printed biosensors in microbiology; A review." *Talanta* 2010; 82:1629-1636, which is incorporated by reference. Additional examples of saliva-based biosensors useable for sensor module 308 can be found at Radha S. P. Malon et al., "Saliva-Based Biosensors: Noninvasive Monitoring Tool for Clinical Diagnostics," *BioMed Research International*, vol. 2014, Article ID 962903, 2014, which is incorporated by reference. An example of an electrochemiluminescence-saliva based biosensor for lactate is discussed by Ballesta Claver, J. "Disposable electrochemiluminescent biosensor for lactate determination in saliva." *Analyst* 2009, 134, 1423-1432, which is incorporated by reference.

Communication device 310 can be in electrical communication with sensor module 308 and/or processing system 312 and can be configured to transmit data in reaction to the output of the sensor. The data can replicate the digital output of sensor module 2018 or provide a processed, and in some embodiments, more simplified signal. Communication device 310 can wirelessly transmit the data to an external device at predetermined periods or when prompted to. Such external devices can include a purpose-built wireless receiver, remote server, smart wearable device, smart phone, smart home device, and/or tablet. In some embodiments, communication is performed via a network connection through a router or other form of direct communication, such as Bluetooth®, Bluetooth LE®, or WiFi Direct®.

Saliva sampling device 302 can include one or more processors, such as low-level processors to handle relatively simple tasks such as sensor monitoring and high-level processors to handle more complex tasks such as data management and communications. These processors can communicate with each other and other components of saliva sampling device 302 to function as processing system 312. In some embodiments, a low-level processor can be capable of functioning independently of a high-level processor. Processing system 312 can be configured to analyze an amount of time the condition is detected by sensor module 308. Processing system 110 can create a record of the amount of time the condition is detected by sensor module 120. An example of a processing and wireless communication system on an oral device is disclosed in Kim et al. "Wearable salivary uric acid mouthguard biosensor with integrated wireless electronics." *Biosensors & bioelectronics* vol. 74 (2015): 1061-8, which is incorporated by reference.

Saliva sampling device 302 can include battery-based power source and/or line power source. In some embodiments, the line power source can be used for charging the battery-based source. Line power source can represent a port (e.g., USB port) and a removable wired connection (e.g., USB cable) and/or an inductive charging module that provides DC power from an external source (e.g., AC/DC wall plug, USB port). In some embodiments, the line power source is provided wirelessly (e.g., wifi, Bluetooth).

Figure 4C:
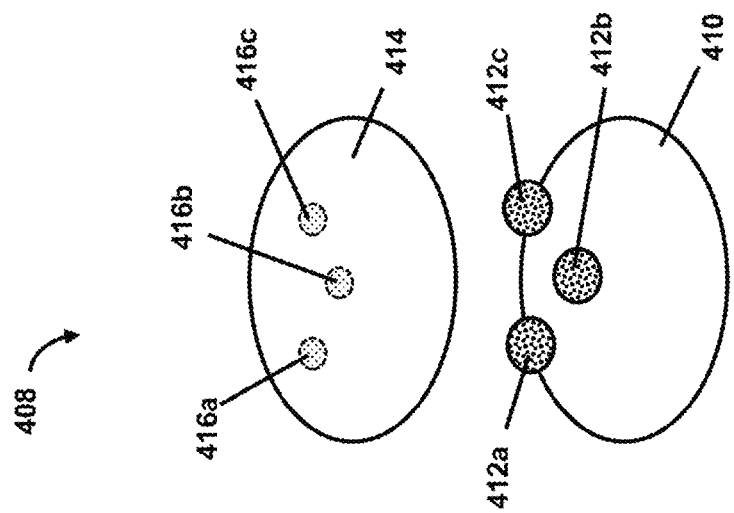
FIG. 4C illustrates an exploded view of a material stack, according to some embodiments.
Figure 4B:
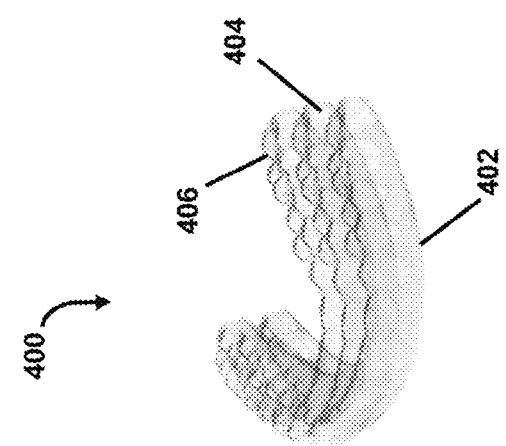
FIG. 4B illustrates an exploded view of a saliva sampling device, according to some embodiments.
Figure 4A:
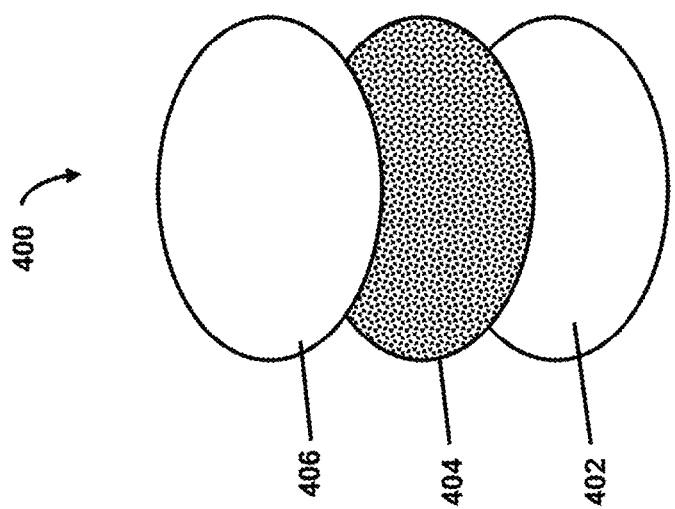
FIG. 4A illustrates an exploded view of a material stack, according to some embodiments.

FIG. 4A illustrates an exploded view of a material stack 400 that can be formed (e.g. thermoformed) into a saliva sampling device, according to some embodiments. Material stack 400 can include base layer 402, sampling layer 404, and top layer 406. In some embodiments, each of the layers is separated prior to forming into a saliva sampling device. In some embodiments, two or all the layers are permanently attached (e.g., bonding, coextruding) to form a single composite layer prior to forming into a saliva sampling device. Base layer 402 and top layer 406 can be thermoformable polymer materials, and each can have single or multiple layers.

Material stack 400 being formed from thermoformable polymer materials can be advantageous because it allows for use of known and easily acquired aligner and retainer formation methods, and hence can be produced at the point of care. An exploded view of each of the base layer 402, sampling layer 404, and top layer 406 is shown at FIG. 4B, after trimming excess material from each formed layer. It should be understood construction of saliva sampling devices is not limited to thermoforming and that other techniques (e.g. 3D printing, casting) can be used.

In some embodiments, the layers can have thicknesses ranging from 0.001-0.035 inches thick, and can be constructed from a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate or a combination thereof.

In some embodiments, one or both of base layer 402 and top layer 406 can include openings (e.g., storage access locations 306) for providing fluidic communication to sampling layer 404. Such openings can be microfluidic in nature and/or be uniformly or non-uniformly located on the layers. In some embodiments, base layer 402 and top layer 406 do not include openings and a fluidic path to sampling layer 404 begin from edges of base layer 402 and top layer 406, which can be connected at discrete points or almost connected except for one or more discrete openings for fluid to pass through.

Sampling layer 404 can include one or more of the sampling aspects disclosed herein, such as described with reference to saliva sampling device 102 and 300. In some embodiments, sampling layer 404 includes a thermoplastic material as a base substrate for carrying additional aspects. For example, in some embodiments, sampling layer 404 can include one or more of: a microfluidic circuit, a channel, chamber, screen printed aspect, screen printed electrical circuit, sample storage portion, communication device, power source, sensor, biosensor, and/or an absorptive portion attached or formed (e.g., by lithography, etching, printing, and/or bonding) the substrate.

In some embodiments, sampling layer 404 does not include a thermoplastic material as a base substrate for carrying additional aspects. For example, sampling layer 404 can be constructed from a highly flexible material, such as silicone, cloth, cellulose, and/or a composite material. In some embodiments, sampling layer 404 can be bonded to one or both of base layer 402 and top layer 406. In some embodiments, base layer 402 and top layer 406 can contain sampling layer 400 by being connected at the outer edges of base layer 402 and top layer 406.

It should be understood that aspects of material stack 400 are optional or limiting. For example, in some embodiments, one or both of base layer 402 and top layer 406 are not required. In some embodiments, additional polymer and/or sampling layers can be used. In some embodiments, sampling layer 404 is the only layer required to form material stack 400 into a saliva sampling device. In addition, although sampling layer 404 is depicted as being continuous in size with base layer 402 and top layer 406, such dimensioning is not required.

In some embodiments, sampling layer 404 is non-continuous with respect to additional layers. An example of this is shown at FIG. 4C which illustrates material stack 408. Material stack 408 shares many of the same aspects and options of material stack 400, which are not repeated here for the sake of brevity. Material stack 408 includes base layer 410, storage portions 412a-c, and top layer 414, which includes storage access locations 416a-c. As shown, storage portions 412a-c are discrete from one another and each has a corresponding storage access location 416a-c for fluidic communication with the oral cavity. Storage access locations 416a-c can include openings (e.g. microfluidic sized openings) for providing fluidic communication from the oral cavity to storage access location 416a-c.

Storage portions 412a-c can have the same aspects as described with respect to sampling layer 404, however, storage portions 412a-c do not have to be identical and therefore each can have different aspects, (e.g., biosensors, circuits, absorptive qualities, etc.). Likewise, storage access locations 416a-c do not have to be identical and therefore each can have different aspects (e.g., number and/or size of openings).

In some embodiments, storage access locations 416a-c can be covered with a user removable cover, which the user can remove to enable sampling at different time periods. In some embodiments, to provide saliva samples at different periods of time, a plurality of bioabsorbable covers can cover a plurality of discrete storage access locations 416a-c and have different thicknesses and/or properties such that the covers erode/absorb at different points during use, e.g., 1 hour, 12 hours, 48 hours, etc. In some embodiments, one ore more of the storage access location 416a-c can be located so as to be placed most proximate to one of the parotid, submandibular, and sublingual glands when worn in the oral cavity. In some embodiments, storage access locations are not included on top layer 414, but rather on bottom layer 410. In some embodiments, storage access locations are only included on bottom layer 410. In some embodiments, neither bottom layer 410 and top layer 414 include storage access locations, and fluidic communication to storage portions 412a-c occurs at the edges of bottom layer 410 and top layer 414.

Figure 5:
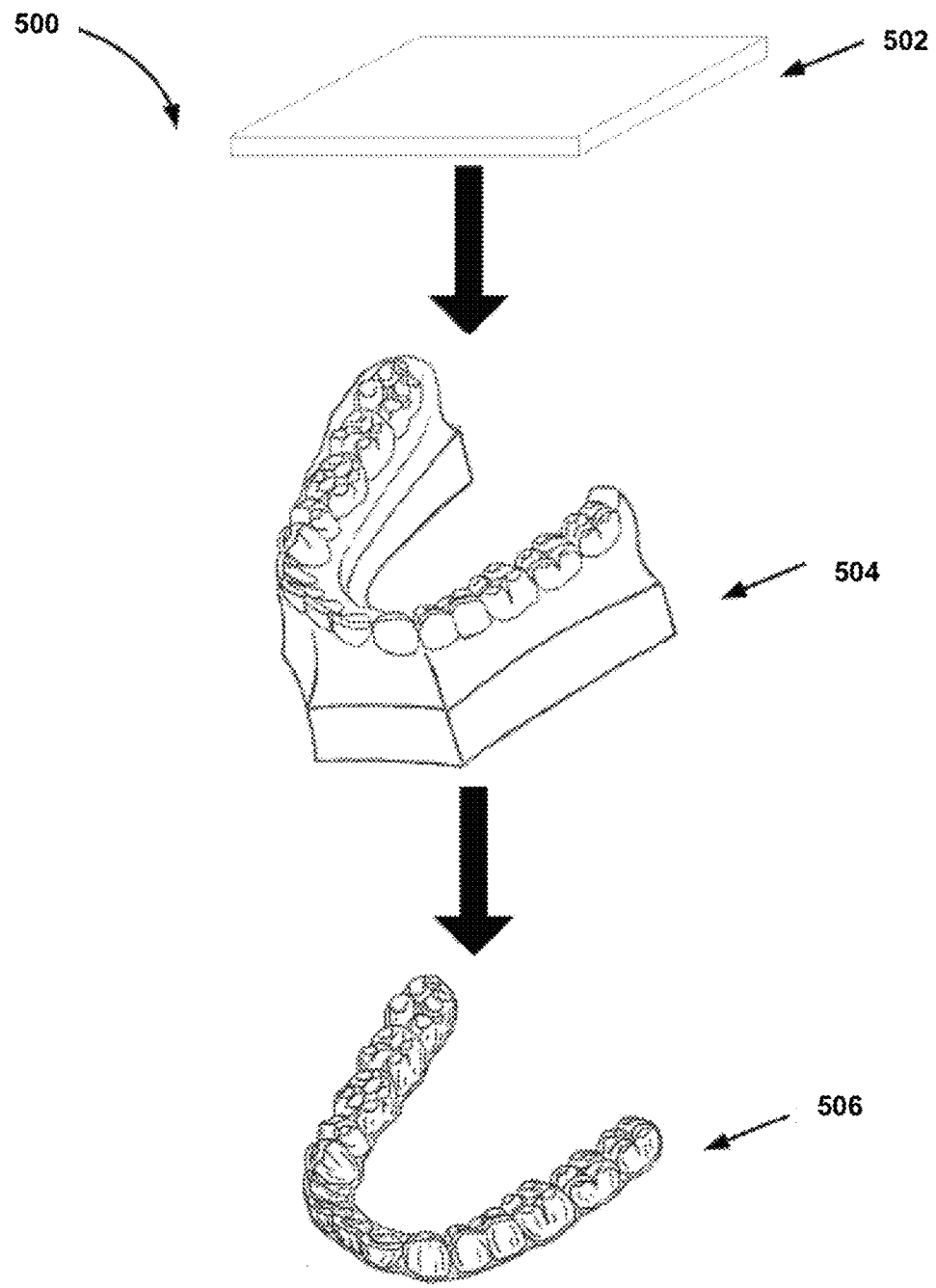
FIG. 5 illustrates a process for forming a saliva sampling device, according to some embodiments.

FIG. 5 depicts an example of a basic process 500 for forming an orthodontic appliance. As shown, a material 502 can be formed into a portion of saliva sampling device 500, which in some embodiments can also function as an orthodontic aligner or an orthodontic retainer. The material 502 can be of one layer to form a single, or only, shell of saliva sampling device 500 or multiple non-affixed layers of material to form multiple shells at once. In some embodiments, material 502 can be one or more layers of material stack 400 and 408. In this example process, the saliva sampling device 500 can be produced with the use of a physical tooth model, or mold, 504. The saliva sampling device 500 can be produced by heating material 502 and then vacuum or pressure forming the material over the teeth in physical tooth model 504. The saliva sampling device 500 is a direct representation of the physical tooth model.

After formation, layers can be affixed to one another according to the desired working elasticity required for the patient. Methods of fixation include chemical bonding, localized melting, fasteners, and/or localized physical deformation key the shells together. Before or after fixation takes place, excess material from the sheet can be trimmed to form a final tooth positioning appliance that can be used for orthodontic treatment of a patient. Some or all of the edges of the layers can be sealed with a flexible material such as silicone to prevent liquid intrusion.

Figure 6:
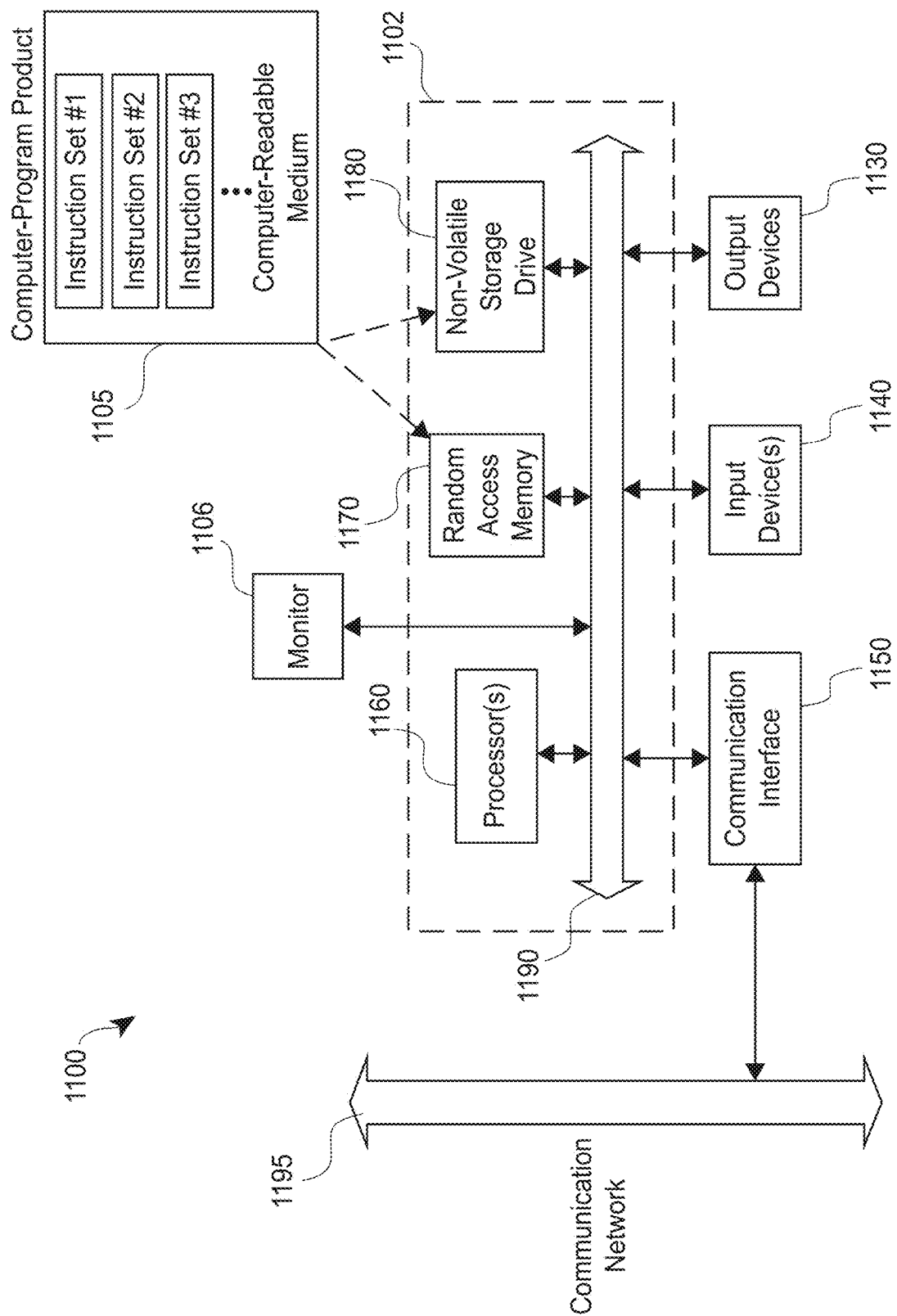
FIG. 6 illustrates a schematic drawing of a computer system, according to some embodiments.

With reference to FIG. 6, an embodiment of a special-purpose computer system 1100 is shown. For example, one or more intelligent components, processing system 110 and components thereof may be a special-purpose computer system 1100. Such a special-purpose computer system 1100 may be incorporated in part or whole as part of a saliva sampling device and/or any of the other computerized devices discussed herein, such as a remote server, mobile device, or network. The above methods may be implemented by computer-program products that direct a computer system to perform the actions of the above-described methods and components. Each such computer-program product may comprise sets of instructions (codes) embodied on a computer-readable medium that direct the processor of a computer system to perform corresponding actions. The instructions may be configured to run in sequential order, or in parallel (such as under different processing threads), or in a combination thereof. After loading the computer-program products on a general-purpose computer system 1126, it is transformed into the special-purpose computer system 1100.

Special-purpose computer system 1100 comprises a computer 1102, a monitor 1106 coupled to computer 1102, one or more additional user output devices 1130 (optional) coupled to computer 1102, one or more user input devices 1140 (e.g., keyboard, mouse, track ball, touch screen) coupled to computer 1102, an optional communications interface 1150 coupled to computer 1102, a computer-program product 1105 stored in a tangible computer-readable memory in computer 1102. Computer-program product 1105 directs computer system 1100 to perform the above-described methods. Computer 1102 may include one or more processors 1160 that communicate with a number of peripheral devices via a bus subsystem 1190. These peripheral devices may include user output device(s) 1130, user input device(s) 1140, communications interface 1150, and a storage subsystem, such as random-access memory (RAM) 1170 and non-volatile storage drive 1180 (e.g., disk drive, optical drive, solid state drive), which are forms of tangible computer-readable memory.

Computer-program product 1105 may be stored in non-volatile storage drive 1180 or another computer-readable medium accessible to computer 1102 and loaded into random access memory (RAM) 1170. Each processor 1160 may comprise a microprocessor, such as a microprocessor from Intel® or Advanced Micro Devices, Inc.®, or the like. To support computer-program product 1105, the computer 1102 runs an operating system that handles the communications of computer-program product 1105 with the above-noted components, as well as the communications between the above-noted components in support of the computer-program product 1105. Exemplary operating systems include Windows® or the like from Microsoft Corporation, Solaris® from Sun Microsystems, LINUX, UNIX, and the like.

User input devices 1140 include all possible types of devices and mechanisms to input information to computer 1102. These may include a keyboard, a keypad, a mouse, a scanner, a digital drawing pad, a touch screen incorporated into the display, audio input devices such as voice recognition systems, microphones, and other types of input devices. In various embodiments, user input devices 1140 are typically embodied as a computer mouse, a touch screen, wireless remote, a drawing tablet, or a voice command system. User input devices 1140 typically allow a user to select objects, icons, text and the like that appear on the monitor 1106 via a command such as a click of a button or the like. User output devices 1130 include all possible types of devices and mechanisms to output information from computer 1102. These may include a display (e.g., monitor 1106), printers, non-visual displays such as audio output devices, etc.

Communications interface 1150 provides an interface to other communication networks, such as communication network 1195, and devices and may serve as an interface to receive data from and transmit data to other systems, WANs and/or the Internet. Embodiments of communications interface 1150 typically include an Ethernet card, a modem (telephone, satellite, cable, ISDN), a (asynchronous) digital subscriber line (DSL) unit, a FireWire® interface, a USBC® interface, a wireless network adapter, and the like. For example, communications interface 1150 may be coupled to a computer network, to a FireWire® bus, or the like. In other embodiments, communications interface 1150 may be physically integrated on the motherboard of computer 1102, and/or may be a software program, or the like.

RAM 1170 and non-volatile storage drive 1180 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1170 and non-volatile storage drive 1180 may be configured to store the basic programming and data constructs that provide the functionality of various embodiments of the present invention, as described above.

Software instruction sets that provide the functionality of the present invention may be stored in RAM 1170 and non-volatile storage drive 1180. These instruction sets or code may be executed by the processor(s) 1160. RAM 1170 and non-volatile storage drive 1180 may also provide a repository to store data and data structures used in accordance with the present invention. RAM 1170 and non-volatile storage drive 1180 may include a number of memories including a main random-access memory (RAM) to store instructions and data during program execution and a read-only memory (ROM) in which fixed instructions are stored. RAM 1170 and non-volatile storage drive 1180 may include a file storage subsystem providing persistent (non-volatile) storage of program and/or data files. RAM 1170 and non-volatile storage drive 1180 may also include removable storage systems, such as removable flash memory.

Bus subsystem 1190 provides a mechanism to allow the various components and subsystems of computer 1102 to communicate with each other as intended. Although bus subsystem 1190 is shown schematically as a single bus, alternative embodiments of the bus subsystem may utilize multiple busses or communication paths within the computer 1102.

Throughout the foregoing description, and for the purposes of explanation, numerous specific details are set forth in order to provide a thorough understanding of the described techniques. It will be apparent, however, to one skilled in the art that these techniques can be practiced without some of these specific details. Although various embodiments that incorporate these teachings have been shown and described in detail, those skilled in the art could readily devise many other varied embodiments or mechanisms to incorporate these techniques. Also, embodiments can include various operations as set forth above, fewer operations, or more operations; or operations in an order. Accordingly, the scope and spirit of the invention should be judged in terms of the claims, which follow as well as the legal equivalents thereof.

The invention claimed is:

1. A health monitoring system comprising:
one or more processors;
memory coupled to the one or more processors, the memory comprising instructions, which when executed by the one or more processors, cause the one or more processors to:
receive data for at least one analyte sourced from at least one saliva sample collected by a saliva sampling device configured to be orally worn by a patient, wherein the saliva sampling device comprises one of: a polymer retainer and a polymer aligner;
correlate the at least one analyte of the at least one saliva sample with at least one health attribute, wherein the at least one saliva sample is collected by the saliva sampling device over a plurality of days during incremental wearing periods of the saliva sampling device by the patient, wherein the at least one saliva sample is collected by the saliva sampling device at one or more time periods initiated by user action with the saliva sampling device that enables sampling of saliva, wherein the user action comprises at least one selected from the group consisting of: removal of a cover on a storage access location on the saliva sampling device, and application of force to the saliva sampling device; and
update a health profile of the patient based on the at least one health attribute.

2. The system of claim 1, wherein the health profile comprises at least one profile for at least one health condition, and wherein the at least one health attribute is used to update the at least one status profile.

3. The system of claim 1, wherein the health profile comprises at least one risk profile for at least one disease, and wherein the at least one correlated attribute is used to update the at least one risk profile.

4. The system of claim 1, wherein the health profile comprises at least one nutrition profile for at least one nutritional aspect, and wherein the at least one health attribute is used to update the at least one nutrition profile.

5. The system of claim 1, wherein each of the incremental wearing periods is at least one hour.

6. The system of claim 1, wherein the at least one saliva sample is one of a plurality of saliva samples collected by the saliva sampling device over a plurality of days.

7. The system of claim 1, wherein the at least one health attribute is processed to provide one or more of: nutritional information, disease information, hormone information, and genetic information.

8. The system of claim 7, wherein the nutritional information comprises one or more of: hydration information, PH level information, fluoride information, mineralization information, alcohol information, and microbiome information.

9. The system of claim 8, wherein the disease information comprises one or more of: infectious disease information, cancer information, inflammation information, and virus information.

10. The system of claim 1, wherein the at least one analyte comprises at least one biomarker of the at least one saliva sample.

11. The system of claim 1, wherein the executed instructions further cause the one or more processors to correlate the at least one analyte of the at least one saliva sample with at least one genetic attribute.

12. The system of claim 1, wherein the executed instructions further cause the one or more processors to store the health profile.

13. The system of claim 1, wherein the executed instructions further cause the one or more processors to provide health monitoring updates and/or alerts to at least one access device.

14. The system of claim 1, wherein the saliva sampling device is one of a plurality of saliva sampling devices, and wherein the health profile is updated and maintained from a plurality of correlated health attributes derived from a plurality of saliva samples collected by the plurality of saliva sampling devices.

15. The system of claim 1, wherein the saliva sampling device comprises at least one biosensor.

16. The system of claim 1, wherein the saliva sampling device comprises a plurality of saliva storage portions configured to store the at least one saliva sample over the plurality of days, and wherein the plurality of saliva storage portions comprises at least one saliva storage portion that is enabled by application of force by a user.

17. The system of claim 1, wherein the saliva sampling device comprises at least one communication device configured to wirelessly connect with a network and/or a network access device, wherein the saliva sampling device wireless transmits the data to the one or more processors, the data being indicative or non-indicative of the at least one analyte.

18. The system of claim 1, wherein the user action comprises the application of force to the saliva sampling device by a user.

19. The system of claim 1, wherein the user action comprises the removal of a cover on a storage access location on the saliva sampling device by a user, and wherein the storage access location comprises an opening in a portion of the saliva sampling device.

20. The system of claim 1, wherein the saliva sampling device comprises a plurality of saliva storage portions configured to store the at least one saliva sample over the plurality of days, and wherein each saliva storage portion of the plurality of saliva storage portions is configured to be user enabled by at least one user action selected from the group consisting of: removal of a cover on a storage access location on the saliva sampling device, and application of force to the saliva sampling device.

* * * * *